United States Patent
Gaglin et al.

(10) Patent No.: US 9,106,807 B2
(45) Date of Patent: Aug. 11, 2015

(54) DEVICE FOR NONCONTACT DETERMINATION OF EDGE PROFILE AT A THIN DISK-SHAPED OBJECT

(71) Applicant: KoCoS Automation GmbH, Weimar (DE)

(72) Inventors: Axel Gaglin, Jena (DE); Thomas Becker, Korbach (DE); Frank Richter, Lichtenfells (DE); Bernd Gey, Gera (DE)

(73) Assignee: KoCoS Automation GmbH, Weimar (DE)

( * ) Notice: Subject to any disclaimer, the term of this patent is extended or adjusted under 35 U.S.C. 154(b) by 383 days.

(21) Appl. No.: 13/757,957

(22) Filed: Feb. 4, 2013

(65) Prior Publication Data
US 2013/0215258 A1 Aug. 22, 2013

(30) Foreign Application Priority Data

Feb. 17, 2012 (DE) .......................... 10 2012 101 301

(51) Int. Cl.
*G01N 21/00* (2006.01)
*H04N 7/18* (2006.01)
*G01N 21/95* (2006.01)
*G01N 21/956* (2006.01)
*G01B 11/25* (2006.01)

(52) U.S. Cl.
CPC ................. *H04N 7/18* (2013.01); *G01B 11/25* (2013.01); *G01N 21/9503* (2013.01); *G01N 21/956* (2013.01)

(58) Field of Classification Search
CPC ........ G01B 11/24; G01B 11/08; G01B 11/25; G01N 21/9503; G01N 21/956; G01N 2021/8822; G01N 21/8806; G01N 21/9501
See application file for complete search history.

(56) References Cited

U.S. PATENT DOCUMENTS

| 5,852,413 A | 12/1998 | Bacchi et al. |
| 2003/0169916 A1 | 9/2003 | Hayashi et al. |

(Continued)

FOREIGN PATENT DOCUMENTS

| DE | 286 664 A5 | 1/1991 |
| DE | 10 2004 057 092 A1 | 6/2006 |

(Continued)

OTHER PUBLICATIONS

Sagar, Geoffrey M., Reflex laser profile gage—on-line measurement of hot rolled sections, Iron and Steel Engineer, Aug. 1997, pp. 60-63.

*Primary Examiner* — Michael P Stafira
(74) *Attorney, Agent, or Firm* — Patentbar International, P.C.

(57) ABSTRACT

A device for noncontact determination of the edge profile at a thin disk-shaped object helps determining the edge profile at semiconductor wafers in which exact image recording is not impaired by specular reflections of the edge profile. A plurality of light sources in the form of laser radiation sources each emitting a line-shaped light bundle are arranged so as to be coplanar in a common plane representing a measurement plane oriented orthogonal to a base plane of the object and are directed from different directions to a common intersection of the laser radiation sources in the edge region of the object. A light sheet is formed in the measurement plane and at least one base camera is directed in the base plane lateral to the measurement plane to capture scattered light proceeding from a light line generated by the light sheet when impinging the object edge region.

10 Claims, 4 Drawing Sheets

(56) References Cited

U.S. PATENT DOCUMENTS

| | | |
|---|---|---|
| 2005/0023491 A1 | 2/2005 | Young et al. |
| 2009/0086483 A1 | 4/2009 | Hahn et al. |
| 2009/0201495 A1 | 8/2009 | Hiramoto et al. |

FOREIGN PATENT DOCUMENTS

| | | |
|---|---|---|
| DE | 10 2007 024 525 B4 | 5/2009 |
| DE | 11 2008 000 723 T5 | 1/2010 |

DEVICE FOR NONCONTACT DETERMINATION OF EDGE PROFILE AT A THIN DISK-SHAPED OBJECT

FIELD OF THE INVENTION

The present invention is directed to a device for noncontact determination of the edge profile of a thin disk-shaped object comprising a turntable for rotating the disk-shaped object around an axis of rotation and a measuring arrangement for radial positioning of at least one light source for illuminating an edge region of the disk-shaped object in virtually radial direction to the axis of rotation thereof, and at least one camera for recording the illuminated edge region. The invention is particularly suitable for reliable and highly precise characterization of the edge profile of a wafer.

In semiconductor fabrication, wafers are machined sequentially in a multitude of process steps during the fabrication process. With increasingly higher integration density of the semiconductor structures, the requirements for the quality of the wafers also increase. In the fabrication of wafers enormous expenditures on material and technology can sometimes result at the end of the value chain. It is therefore meaningful and legitimate to subject wafers to extensive testing before processing, i.e., at the beginning of the value chain, so that the wafers can be selected based on the highest reliability and fullest possible utilization of material surfaces. This testing also includes inspection of the outer circumferential edge of a wafer to check for suitable shape and integrity of the circumferential edge. A number of checking devices able to perform these inspections has already been suggested.

BACKGROUND OF THE INVENTION

DE 10 2007 024 525 B4 describes a device in which three cameras are used to perform a visual assessment of defects in the edge region of a wafer. For recording defects, one camera is positioned opposite the edge region above the wafer and one camera is positioned opposite the edge region below the wafer. A third camera is disposed opposite the edge region of the wafer in radial direction. The edge region of the wafer captured by the cameras is illuminated by a homogeneous, diffusely radiating illumination, and pictures are taken by the camera and displayed to a user of the device on a monitor for visual evaluation. Thus it is possible when capturing and using the exact position of a defect on the wafer that subjective assessments of the defects can also be made. An objective, qualitative assessment of defects is not possible in this device.

In an edge checking device disclosed in DE 11 2008 000 723 T5, test results are displayed depending on the edge information acquired from the inspected wafer. For this purpose, the circumferential surface of a wafer is captured from three recording directions by at least one CCD line camera. The axes of the three image recordings intersect in the center plane of the wafer at a point close to the circumferential surface of the wafer so that one viewing direction is directed to the outer circumferential surface and the other two image recordings are directed, respectively, to the beveled circumferential edges of the wafer. The configuration of the illumination needed for image capture was not disclosed. The captured images are displayed on a display device for manual evaluation and the position-dependent edge information is stored in a storage unit. Further, edge information is stored in a storage unit depending on position based on changes in shading in the captured image content. The acquired data are preferably displayed visually in the form of a profile curve on the basis of which a statistical evaluation of the edge information is made possible so that a trend in the overall shape can be determined therefrom. This has the drawback that image defects caused, for example, by reflected light at trouble spots or by improperly angled edge regions when making photographic recordings of a small segment of the edge region of a wafer by means of CCD line cameras can lead to erroneous interpretations of the actual edge shape, can corrupt measurement results or even render measurement impossible.

SUMMARY OF THE INVENTION

Therefore, it is the object of the invention to find a novel possibility for determining an edge profile at thin disk-shaped measurement objects (e.g., semiconductor wafers) which makes it possible during image recording of the edge profile to substantially suppress specular reflections which impede or degrade determination of the edge profile.

In a device for determination of the edge profile at a thin disk-shaped object comprising a turntable for rotating the disk-shaped object around an axis of rotation and a measuring arrangement for radial positioning of at least one light source for illuminating an edge region of the disk-shaped object in virtually radial direction to the axis of rotation thereof, and at least one camera for recording the illuminated edge region, wherein the camera is arranged in a base plane extending parallely and medially between the plane faces of the disk-shaped object, the above-stated object is met in that there is provided a plurality of light sources in the form of laser radiation sources with line-shaped beam profile which each emit a line-shaped light bundle, in that the line-shaped light bundles of the laser radiation sources are arranged so as to be coplanar in a common plane representing a measurement plane oriented orthogonal to the base plane and are directed from different directions to a common intersection of the laser radiation sources in the edge region of the object, wherein a light sheet composed of the line-shaped light bundles of the laser radiation sources is formed in the measurement plane, and in that the at least one camera, as base camera, is directed in the base plane lateral to the measurement plane so that it records scattered light proceeding from a light line illuminated by the light sheet in the edge region of the object.

The laser radiation sources are advantageously arranged in such a way that the line-shaped light bundles thereof illuminate the edge region of the disk-shaped object so as to surround it in a U-shaped manner. In this respect, it is useful to arrange three laser radiation sources in such a way that a base laser radiation source is arranged in the base plane and two further laser radiation sources are arranged (symmetric to the two sides of the base laser radiation source) in the measurement plane at an irradiation angle of equal size but different mathematical sign and are directed to the common intersection.

For alignment of the base camera, it is advantageous that an observation angle between the base camera and the base laser radiation source in the base plane is adjustable in the range between 30° and <90°.

In addition to the base camera, it is advisable that two further cameras are directed lateral to the measurement plane and to the intersection of the optical axes of the laser radiation sources, preferably at the same pitch angle perpendicular to or under the base plane in each instance, to improve the resolution of the image recording.

Further, it proves advantageous to provide a notch camera in addition to the base camera, the optical axis of the notch camera being arranged in the base plane at a latitude angle to the base laser radiation source that is substantially smaller than the observation angle of the base camera to the base laser radiation source.

To adjust the measuring arrangement to different diameters of disk-shaped objects and to compensate for eccentricity in a rotating edge profile, a linear guide is advisably provided for moving the measuring arrangement orthogonal to the axis of rotation of the turntable.

A centering camera oriented perpendicular to the base plane is advantageously provided for detecting an eccentric position of the edge region of the disk-shaped object relative to the axis of rotation of the turntable and is arranged outside the measurement plane defined by the laser radiation sources. The radial position of the centering camera can be adjusted to a diameter of the object that is known beforehand, and the centering camera is arranged opposite a diffuse illumination unit. For this purpose, it is advisable that the angular position of the centering camera to the measurement plane, which angular position is adjusted in the base plane, is provided for calculating a tracking movement of the measuring arrangement which compensates for eccentricity.

For vibration-decoupled measurement, a solid base plate is advantageously used as a component carrier for a table system with the turntable, for a linear guide and a supporting system for the measuring arrangement and for additional elements of the device.

The invention is based on the fundamental consideration that because of interfering reflections a purely optical generation and observation of images of the edge profile leads to a flawed acquisition of at least some portions of the edge profile of wafers. The invention solves this problem by selecting a camera arrangement which records exclusively scattered light from the object edges and in that the scattered light is captured lateral to an illumination plane generated by line-shaped illumination. The illumination is preferably carried out by means of line lasers which impinge from different directions so as to generate a thin planar light sheet (light curtain) into which the profile of the object to be measured intrudes and is moved orthogonally through the latter. The line lasers generate a homogeneous laser line on the measurement object, which laser line is illuminated by line lasers impinging in a coplanar manner orthogonally on the edge profile to be measured. As a result of this light curtain impinging "on all sides", virtually every point of the edge region of the measurement object is illuminated orthogonally and an intensive, narrowly spatially defined fringe of light is generated around the end profile during lateral image recording by the camera arrangement so that the edge profile is progressively imaged planewise due to the orthogonal movement of the edge profile through the light curtain.

The images which are successively recorded by the camera arrangement and which have no superposition errors or distortion in spite of a plurality of light sources allow a more precise measurement of edge(s) compared to previously known solutions. This happens because when the edge profile penetrates into the light sheet, a uniform intensive laser line is generated along the edge profile and a light fringe thereof which is generated by scattered light is recorded by the camera arrangement lateral to the light sheet and can be objectively evaluated by means of software. It should be noted that the light fringe of the light sheet impinging on the measurement object "on all sides" is also referred to herein interchangeably as "light line" to simplify the description of the image recordings of the profile of the measurement object.

The device makes it possible to determine the edge profile at thin disk-shaped measurement objects quickly and reliably, and a reflection-free, highly precise recording of the edge profile is achieved even when trouble spots or improperly angled object edges are found in the edge profile.

BRIEF DESCRIPTION OF THE DRAWINGS

The invention will be described more fully in the following with reference to embodiment examples. The drawings show.

DETAILED DESCRIPTION OF THE PREFERRED EMBODIMENTS

Figure 1:
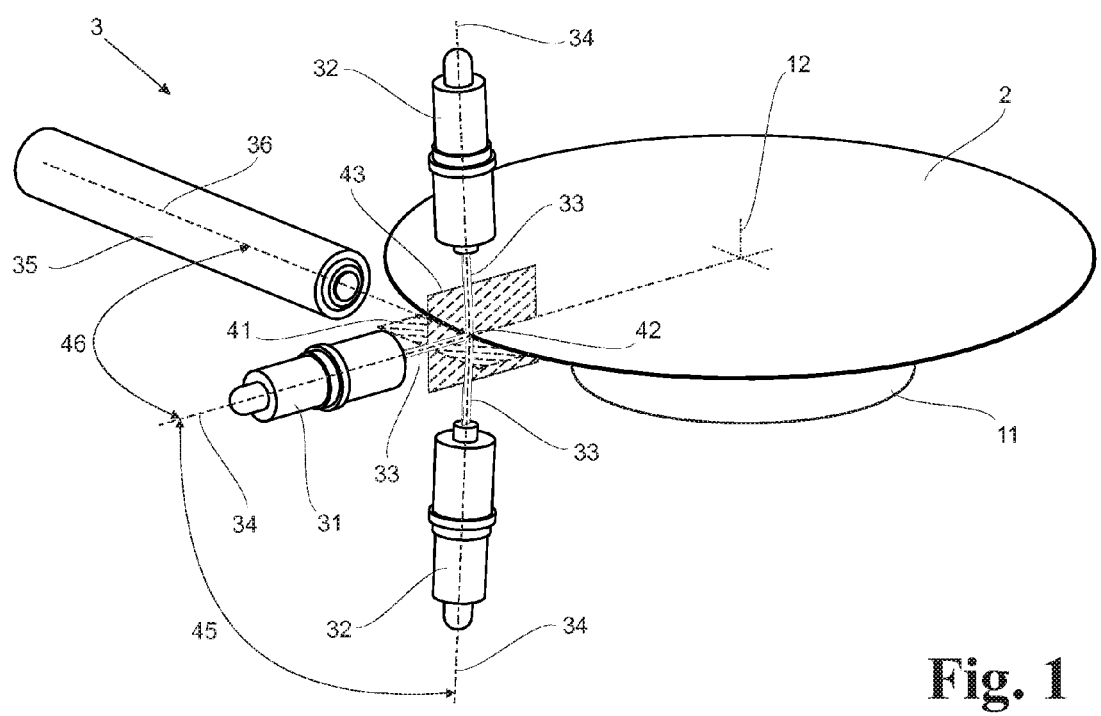
FIG. 1 a schematic construction of the device according to the invention.

According to FIG. 1, the device has a measuring arrangement 3 including a base laser radiation source 31, at least two further laser radiation sources 32 and at least one base camera 35. The optical axis 34 of the base laser radiation source 31 and the optical axis 36 of the base camera 35 are arranged substantially orthogonal to one another in a preferably horizontally oriented common base plane 41 and meet at an intersection 42. The further laser radiation sources 32 are arranged with their optical axes 34 symmetric to both sides of the base laser radiation source 31 in a measurement plane 43 at an irradiation angle 45 of the same size but different sign relative to the base laser radiation source 31 and are likewise directed into intersection 42. The laser radiation sources 31 and 32 are preferably line lasers of identical construction and have line-shaped beam profiles whose light bundles 33 collectively form a light sheet 4 inside the measurement plane 43. The light sheet 4 has an orthogonal orientation to the base plane 41.

In order that a profile to be measured at a measurement object, which in this case—without limiting generality—is the edge profile 21 of a wafer 2, can be aligned with the components (laser radiation sources 31 and 32 and at least the base camera 35) of the measurement arrangement 3 which are exactly aligned with one another, a table system 1 is arranged at a defined distance from the measuring arrangement 3. The wafer is movably supported by the table system 1 and can be moved through the light sheet 4 along the edge profile 21 to be measured.

Figure 2:
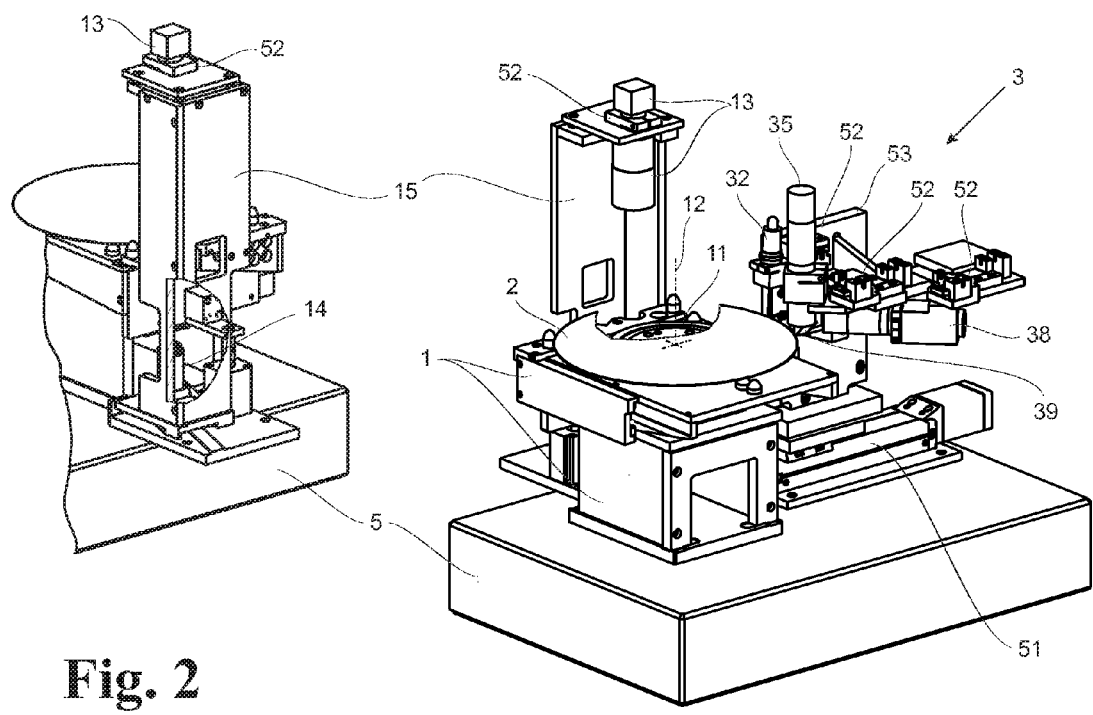
FIG. 2 one specific embodiment form of the device according to the invention in full elevation (right-hand side) and a fragmentary view of the back (left-hand side)

The table system 1 according to FIG. 2 is outfitted with a turntable 11 for the wafer 2 which is provided in this example as measurement object. The turntable 11 has a horizontal support surface supporting the wafer 2. The axis of rotation 12 of the turntable 11 is oriented orthogonal to the base plane 41.

According to FIG. 2, a linear guide 51 is provided on a base plate 5 for receiving the measuring arrangement 3. The linear guide 51 is oriented in such a way that the measuring arrangement 3 is arranged with its intersection 42 of the optical axes 34 and 36 of laser radiation sources 31, 32 and of base camera 35, respectively, displaceably in an orthogonal direction relative to the axis of rotation 12 of the turntable 11 in the base plane 41. The optical axis 34 of the base laser radiation source 31 is arranged parallel to the movement direction of the linear guide 51 so that the line-shaped light bundle 33 of the base laser radiation source 31 is oriented substantially in a radial plane to the axis of rotation 12 of the turntable 11.

To achieve the highest possible accuracy with the device, a solid granite block with a moment of inertia adapted to the maximum acceleration forces of the turntable 11, linear guide 51 and table system 1 is used as base plate 5. The base plate 5 is supported so as to be decoupled from vibrations relative to the substrate at the installation site.

As is shown in FIG. 2, the wafer 2 with an edge profile 21 to be inspected is placed so as to be as centered as possible with one of its plane faces on the support surface of the turntable 11. The support surface has a smaller diameter than the wafer 2 to be measured so that the entire edge region 22 of the wafer 2 freely projects beyond the edge of the turntable 11. The support surface of the turntable 11 can be adapted to commercial wafer sizes in a corresponding manner for optimal accommodation of various wafer sizes.

Figure 3:
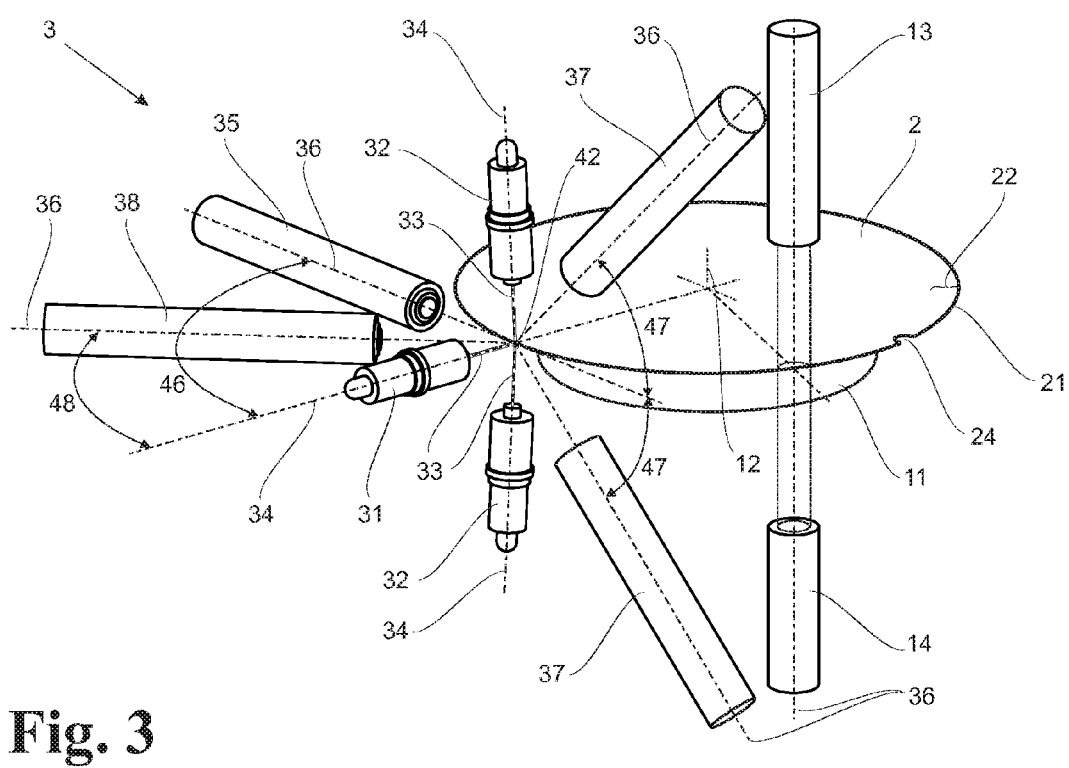
FIG. 3 a schematic construction of the device according to the invention in a preferred embodiment with four cameras for edge recording and with an additional unit for detecting eccentricity.

The wafer 2 can be set in rotation with the turntable 11. Inaccuracies in the positioning of the wafer 2 resulting in an eccentricity between the wafer axis and the axis of rotation 12 of the turntable 11 are captured by a centering camera 13. For this purpose, as is shown in FIG. 3, the centering camera 13 is positioned above the support surface of the turntable 11 over the wafer edge region 21. A telecentrically radiating illumination unit 14 which is arranged below the support surface of the turntable 11 radiates a diffuse light in direction of the centering camera 13. With the wafer edge region 22 arranged therebetween, a silhouette of the outer edge 23 of the wafer 2 is generated opposite the centering camera 13. Based on the silhouette, the cyclical movements of the outer edge 23 of the wafer occurring during the rotation of an eccentrically positioned wafer 2 can be captured by the centering camera 13 depending on the angle of rotation and stored. The values acquired in this way are used to control the linear guide 51 in the process of determining the edge profile so as to compensate for the eccentric position of the wafer 2 relative to the intersection 42 of the optical axes 34 and 36 of the measuring arrangement 3 so it is not necessary to correct the eccentric position of the wafer 2 on the turntable 11. To correlate the rotational angle-dependent positional variations of the outer edge 23 of the wafer 2 relative to the intersection 42 of the measuring arrangement 3, it is merely necessary to know the angle formed by the axis of rotation 12 between the intersection 42 and optical axis 36 of the centering camera 13.

A holder 15 shown in FIG. 2 is provided for fastening the centering camera 13 which is situated on the optical axis 34 of the illumination unit 14. Adjustment of the position of the centering camera 13 to the different diameters of commercial wafer sizes is ensured in that the holder 15 is displaceable relative to the turntable 11 in a radial direction relative to the axis of rotation 12.

After acquiring the eccentricity of the wafer 2 and, therefore, the rotation angle-dependent position of the edge profile 21, the measuring arrangement 3 can be moved by means of the linear guide 51 in direction of the turntable 11 out of an idle position at the greatest distance from the turntable 11 into a ready position which is determined based on wafer size. In accordance with the previously measured eccentricity of the supported wafer 2, a rotation angle-dependent signed offset is applied to this ready position. By summing the ready position and offset, the measuring arrangement 3 reaches an inspection position in which the intersection 42 of the optical axes 34 and 36 of the measuring arrangement 3 is always held in a constant position relative to the outer edge 23 of the wafer 2.

Figure 4:
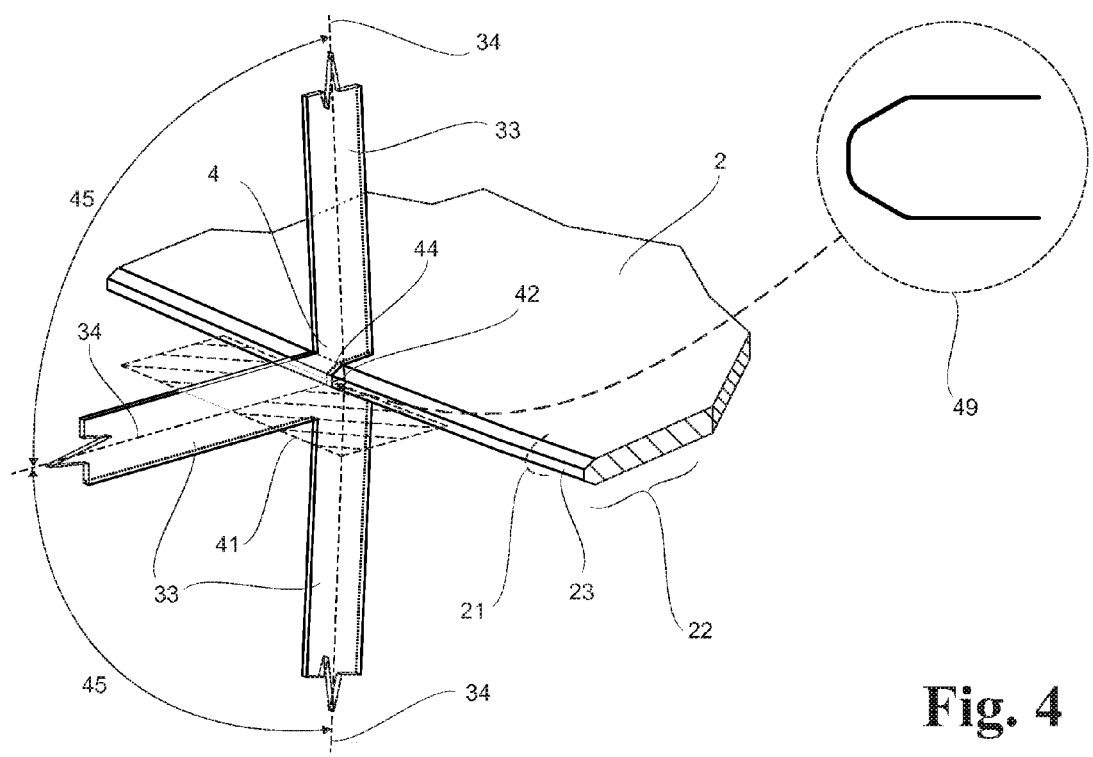
FIG. 4 a schematic illustration of the generation of the light sheet in the region of a wafer edge profile.

As is shown in FIG. 4, the light sheet 4 is formed as measurement plane 43 in orthogonal orientation to the base plane 41 owing to the line-shaped beam profile of the light bundles 33 proceeding from the laser radiation sources 31 and 32. The irradiation angle 45 of the further laser radiation sources 32 can have a value ranging between 10° and 90° to the base laser radiation source 31 depending upon requirements. Therefore, the light bundles 33 of the further laser radiation sources 32 always impinge on the edge region 22 of the wafer 2 from a position arranged below and above the plane faces of the wafer 2 so that a light line 44 enclosing the edge profile 21 in a U-shaped manner is illuminated on the edge region 32 of the wafer 2 when the wafer 2 penetrates the light sheet 4. If the irradiation angle 45 of the laser radiation sources 32 is in the range of 45° or less, the base laser radiation source 31 can be dispensed with.

The scattered light proceeding from the light line 44 can be captured in the form of a light fringe by the base camera 35 which is arranged in the base plane 41 and which operates telecentrically. This light fringe "seen" by the base camera 35 is shown in FIG. 4 in an enlarged section (upper right) as a stylized image recording 49 of the base camera 35.

By capturing the scattered light emanating from the light line 44 at the edge profile 21 and through a procedure which is already known from light section methods as they are called, the surfaces of the edge region 22 of the wafer 2 and especially the outer edge 23 of the wafer 2 can be inspected and any anomaly, e.g., divergent shape or mechanical damage, can be recorded. In order to capture the edge profile 21 with high spatial resolution, the light sheet 4 has a thickness, and therefore the light line 44 has a width, between 1 μm and a maximum of 25 μm.

To capture the scattered light of the light line 44, the base camera 35 with a high-resolution objective is secured in the measuring arrangement 3. Its optical axis 36 is arranged in the base plane 41 at an observation angle 46 to the optical axis 34 of the base laser radiation source 31. The working distance of the base camera 35 is selected in such a way that the light sheet 4 is located exactly in the depth of focus range of the objective of the base camera 35. Since as a general rule there are no further elements in the edge region 22 of the wafer 2 which mask the scattered light in the base plane 41, the observation angle 46 between the base camera 35 and the base laser radiation source 31 can be selectively adjusted within a very wide range between 30° and <90°.

In order to achieve a more compact construction of the measuring arrangement 3, the base camera 35 can also be arranged perpendicularly as is shown in FIG. 2; for this purpose, a deflecting prism 39 is arranged in front of the objective of the base camera 35. In this case, to capture the scattered light of the light line 44 the deflecting prism 39 is arranged exclusively in the base plane 41 in order to direct the angled optical axis 36 of the base camera 35 in the intersection 42 tangential to the outer edge 23 of the wafer 2.

The edge profile 21 of the wafer 2 rotating by means of the turntable 11 continuously passes through the light sheet 4. The reflections of the light line 44 projected on the edge profile 21 are acquired by the base camera 35 only in the form of a scattered light distribution. The corresponding rotation angle of the wafer 2 is captured at the same time based on the position of the turntable 11. In this way, the captured scattered light distribution can also be associated with an unambiguous position on the edge region 22 of the wafer 2, the local edge profile 21 can be acquired by assessing the characteristic features of the scattered light distribution, and every trouble spot on the edge profile 21 of the wafer 2 can be recorded and stored.

If the scattered light of the light line 44 is observed at a defect-free wafer edge region 22, the greatest intensity of scattered light that is recorded corresponds to a perspective edge profile 21 within the radial plane of the wafer 2 through the intersection 42 defining the measurement plane 43. Every profile deviation or damage to the edge region 22 of the wafer 2 changes the extent, structure and intensity of the scattered light and therefore provides information about characteristic surface changes deviating from an expected standard shape.

By means of the known observation angle 46 between the base camera 35 and base laser radiation source 31 and the known rotation angle of the wafer 2 on the turntable 11, the position and magnitude of changes to the requisite edge profile 21 can be detected in a very precise manner. The position data which are determined in this way are converted into a digital blank profile and used to determine the edge profile 21 by applying appropriate algorithms. The data of the edge profile 21 can be evaluated within the framework of quality assurance or sent to appropriate machines for carrying out subsequent edge machining.

With highly reflective surfaces such as are found in polished metals or semiconductor substrates, reflections may occur during the inspection of an edge profile 21 which interfere with a reliable detection of the scattered light by an individual base camera 35. In order to achieve a reliable detection of the edge profile 21 of a wafer 2 in the edge region 22 thereof also under reflective surface conditions of this kind, further cameras 37 can be used in addition to the base camera 35.

For this purpose, as is shown in FIG. 3, two additional cameras 37 are arranged above and below the base plane 41 in a tangential plane extending through the optical axis 36 of the base camera 35 and oriented orthogonal to the base plane 41 and are directed to the intersection 42. The two additional cameras 37 have the same pitch angle 47 and, therefore, a symmetrical arrangement with respect to the base plane 41. The pitch angle 45 is preferably 45° but can also be adjusted in the range between 10° and 90° in principle.

To identify the crystal orientation in silicon wafers, the edge region 22 of the wafer 2 is usually provided with at least one notch 24. As a result of the standardized notch 24, when traversing the light sheet 4 neither the base camera 35 nor the additional cameras 37 can capture portions of the light line 44 at the deeper points of the notch 24 because they are partially concealed by the regular edge profile 21 of the edge region 22 of the wafer 2. It is useful to employ an additional notch camera 38 so that the edge profile 21 of the outer edge 23 of the wafer 2 can also be fully captured in this area as well.

To this end, the notch camera 38 is arranged with its optical axis 36 in the base plane 41 and in a latitude angle 48 of preferably 45° to the optical axis 34 of the base laser radiation source 31. The latitude angle 48 can also be adjusted so as to diverge from 45° provided the notch camera 38 can still capture the scattered light of the light line 44 uninterruptedly in the entire region of the notch 24. The precisely acquired position of the notch 24 can also be used in combination with the angle of rotation of the turntable 11 as a reference point for associating the angle of rotation with the successively acquired image recordings of the light line 44 of the edge profile 21 of the wafer 2.

The objectives of the base camera 35, of all of the additional cameras 37 and of the notch camera 38 are configured confocally, i.e., the focal points thereof lie exactly in the light sheet 4 at the intersection 42 of the optical axes 34 and 36 of the base laser radiation source 31 and base camera 35 and accordingly correspond to the desired point of incidence of the base laser radiation source 31 on the outer edge 23 of the wafer 2. As is shown in FIG. 2, the alignment of the cameras 35, 37 and 38 and of the laser radiation sources 31 and 32 is carried out by means of precisely adjustable fastening elements 52 which are arranged at a supporting system 53 for the measuring arrangement 3, this supporting system 53 being moved by means of the linear guide 51, and the cameras 35, 37 and 38 and laser radiation sources 31 and 32 of the measuring arrangement 3 can be adjusted and fixed in a defined manner relative to one another by means of these fastening elements 52. As a result of this arrangement and the known angles between the light sheet 4, base plane 41 and camera positions for defining the measurement plane 43, the recordings of the scattered light of the light line 44 made by the individual cameras 35, 37 and 38 along the edge profile 21 of the wafer 2 are superposed without distortion, and a very precise edge profile 21 of the edge region 22 of the wafer 2 can be calculated therefrom. This makes possible a reliable and precise characterization of the edge profile 21 of a wafer 2.

LIST OF REFERENCE NUMERALS 1 table system
11 turntable
12 axis of rotation
13 centering camera
14 illumination unit
15 holder
2 wafer
21 edge profile
22 wafer edge region
23 outer edge of the wafer
24 notch
3 measuring arrangement
31 base laser radiation source
32 additional laser radiation source
33 light bundle
34 optical axis (of the light source)
35 base camera
36 optical axis (of the base camera)
37 additional camera
38 notch camera
39 deflecting prism
4 light sheet
41 base plane
42 intersection
43 measurement plane
44 light line
45 irradiation angle
46 observation angle
47 pitch angle
48 latitude angle
49 image recording (of the base camera)
5 base plate
51 linear guide
52 fastening element
53 supporting system (of the measuring arrangement)

What is claimed is:

1. A device for noncontact determination of an edge profile at a disk-shaped object, the device comprising:
   a turntable for rotating the disk-shaped object around an axis of rotation and a measuring arrangement for radial positioning of at least one light source for illuminating an edge region of the disk-shaped object in a virtually radial direction to the axis of rotation thereof;
   at least one camera for recording the illuminated edge region, the camera being arranged in a base plane extending parallely and medially between the plane faces of the disk-shaped object;
   a plurality of laser radiation light sources with a line-shaped beam profile, each laser radiation source emitting a line-shaped light bundle, the plurality of laser radiation sources forming line-shaped light bundles arranged to be coplanar in a common plane representing a measurement plane oriented orthogonal to a base plane, the line-shaped light bundles being directed from different directions to a common intersection in the illuminated edge region of the object; and a light sheet comprised of the line-shaped light bundles formed in the measurement plane;

wherein the at least one camera serving as a base camera is directed to the base plane laterally to the measurement plane, so that the at least one camera records scattered light propagating from a light line illuminated by the light sheet in the edge region of the object.

2. The device according to claim 1, wherein the laser radiation sources are arranged in such a way that the line-shaped light bundles illuminate the edge region in a U-shaped manner.

3. The device according to claim 2, wherein the laser radiation sources comprise a base laser radiation source arranged in the base plane and wherein two additional laser radiation sources arranged symmetrically to two sides of the base laser radiation source in the measurement plane at two equal but opposite irradiation angles and two additional laser sources are directed to the common intersection.

4. The device according to claim 1, wherein an observation angle between the base camera and a base laser radiation source in the base plane is adjustable in the range between 30° and ≤90°.

5. The device according to claim 1, further comprising two further cameras directed laterally to the measurement plane and to the common intersection of optical axes of the laser radiation sources at the same pitch angle above or below the base plane, respectively.

6. The device according to claim 1, further comprising a notch camera, wherein an optical axis of the notch camera being arranged in the base plane at a latitude angle that is substantially smaller than an observation angle of the base camera relative to the measurement plane.

7. The device according to claim 1, further comprising a linear guide for moving the measuring arrangement orthogonally relative to the axis of rotation of the turntable.

8. The device according to claim 1, further comprising a centering camera oriented perpendicularly relative to the base plane for capturing an eccentric position of the edge region relative to the axis of rotation of the turntable, the centering camera being arranged outside the measurement plane, wherein a radial position of the centering camera can be adjusted to a predetermined diameter of the disk-shaped object, and wherein the centering camera is arranged opposite a diffuse illumination unit.

9. The device according to claim 8, wherein an angular position of the centering camera relative to the measurement plane is provided for calculating a tracking movement of the measuring arrangement which compensates for eccentricity, the angular position being adjustable in the base plane.

10. The device according to claim 1, further comprising a solid base plate for vibration decoupled measurements, the base plate being vibration-damped mounted to a substrate at an installation site and serving as a component carrier for a table system with the turntable, for a linear guide and a supporting system of the measuring arrangement and for any elements arbitrarily supplemented to the device.

* * * * *